United States Patent
Brown et al.

(10) Patent No.: US 7,188,731 B2
(45) Date of Patent: Mar. 13, 2007

(54) VARIABLE FLEXURE-BASED FLUID FILTER

(75) Inventors: Steve B. Brown, Livermore, CA (US); Billy W. Colston, Jr., San Ramon, CA (US); Graham Marshall, Fox Island, WA (US); Duane Wolcott, Fox Island, WA (US)

(73) Assignee: The Regents of the University of California, Oakland, CA (US)

( * ) Notice: Subject to any disclaimer, the term of this patent is extended or adjusted under 35 U.S.C. 154(b) by 406 days.

(21) Appl. No.: 10/648,626

(22) Filed: Aug. 25, 2003

(65) Prior Publication Data

US 2004/0074849 A1    Apr. 22, 2004

Related U.S. Application Data

(60) Provisional application No. 60/406,191, filed on Aug. 26, 2002.

(51) Int. Cl.
*B01D 33/01* (2006.01)
*B01D 35/06* (2006.01)
*F16K 1/38* (2006.01)
*B01D 37/00* (2006.01)

(52) U.S. Cl. ............... 210/348; 210/767; 210/350; 210/351; 210/357; 210/352; 417/53; 417/507; 251/331; 251/356

(58) Field of Classification Search ............ None
See application file for complete search history.

(56) References Cited

U.S. PATENT DOCUMENTS

| | | | | |
|---|---|---|---|---|
| 4,506,276 A * | 3/1985 | Kyser et al. | ............... | 347/86 |
| 4,834,534 A * | 5/1989 | Wiget | ............... | 356/246 |
| 6,629,820 B2 * | 10/2003 | Kornelsen | ............... | 417/53 |
| 6,761,270 B2 * | 7/2004 | Carew | ............... | 210/352 |
| 2002/0045287 A1 * | 4/2002 | Gamble et al. | ............... | 438/48 |
| 2003/0038032 A1 | 2/2003 | Reel et al. | | |
| 2003/0066956 A1 | 4/2003 | Gruber et al. | | |

FOREIGN PATENT DOCUMENTS

WO    WO 02/16903 A2    2/2002

* cited by examiner

*Primary Examiner*—Krishnan S. Menon
(74) *Attorney, Agent, or Firm*—Eddie E. Scott

(57) ABSTRACT

An apparatus and method for filtering particles from a fluid comprises a fluid inlet, a fluid outlet, a variable size passage between the fluid inlet and the fluid outlet, and means for adjusting the size of the variable size passage for filtering the particles from the fluid. An inlet fluid flow stream is introduced to a fixture with a variable size passage. The size of the variable size passage is set so that the fluid passes through the variable size passage but the particles do not pass through the variable size passage.

10 Claims, 2 Drawing Sheets

VARIABLE FLEXURE-BASED FLUID FILTER

CROSS-REFERENCE TO RELATED APPLICATIONS

This application claims the benefit of U.S. Provisional Patent Application No. 60/406,191 filed Aug. 26, 2002 and titled "Variable Flexure-Based Fluid Filter." U.S. Provisional Patent Application No. 60/406,191 filed Aug. 26, 2002 and titled "Variable Flexure-Based Fluid Filter" is incorporated herein by this reference.

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to filters and more particularly to fluid filters.

2. State of Technology

There are four broad categories of filtration systems. The first, and most common, employs a matrix-type filter. The matrix-type filter is made of cellulose, polyurethane, and other materials. The matrix-type filter employs various layers of a material that capture particles by providing a tortuous path with a mean physical porosity smaller than the target particles. The biggest drawback of this type of filter is the difficulty in recovering particles once they are trapped. In addition, any single filter can only be used to filter particles above a certain size threshold and cannot be dynamically varied.

The second category can be labeled as physical, non-matrix type filters such as Anapore. These materials provide a planar structure (such as ceramic or silicon) with relatively uniform holes through which fluid can pass, but particles become trapped. Recovery from these filters is possible since the particles do not become embedded in the filter material, as happens with the matrix-type filters. These filters, however, tend to be brittle and have a predetermined particle filter limit (determined by the hole size). In addition, the two dimensional nature of these filters and the need to place them orthogonal to the inlet flow, places practical design constraints on the packaged filter system. These include difficulty in creating a uniform seal around the filter, flow rate limitations dictated by the filter area and pore size, and constraints on the volume of fluid used to recover particles from the filter surface.

The third category of filter uses the dielectric properties of the particles coupled with a magnetic or electrical capture field. Magnetic separation is the most commonly used method in bioanalytical processes. There are several disadvantages to using magnetic beads. Filtration of biologicals such as bacteria, spores, and cells is difficult or impossible since their attraction in electrical or magnetic fields is fairly weak. In addition, this method requires instrumentation (magnets, electrodes, etc.) and design of associated EM fields for capturing particles with a given dielectric property. This precludes the use of many materials (polymers, etc.) that are commonly doped with fluorescent compounds for multiplex analysis in optical based detection modalities such as flow cytometry.

The fourth category is a fixed-gap type filter. This category of filter typically uses precision machining or micro-machining (i.e., silicon etching) methods to create very uniform barriers for trapping particles. The advantage of this method is the ability to create highly reproducible filters with small volume sizes that can be used to both capture and recover particles. The principal disadvantage of this category of filter is the inability to dynamically change the barrier size. In addition, integration and packaging of microfluidic devices is still challenging.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides an apparatus and method for filtering particles from a fluid. In one embodiment an apparatus is provided for filtering particles from a fluid. The apparatus comprises a fluid inlet, a fluid outlet, a variable size passage between the fluid inlet and the fluid outlet, and means for adjusting the size of the variable size passage for filtering the particles from the fluid. In another embodiment a method of filtering particles from a fluid is provided. The method comprises the steps of introducing an inlet fluid flow stream to a fixture with a variable size passage, setting the size of the variable size passage so that the fluid passes through the variable size passage but the particles do not pass through the variable size passage.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
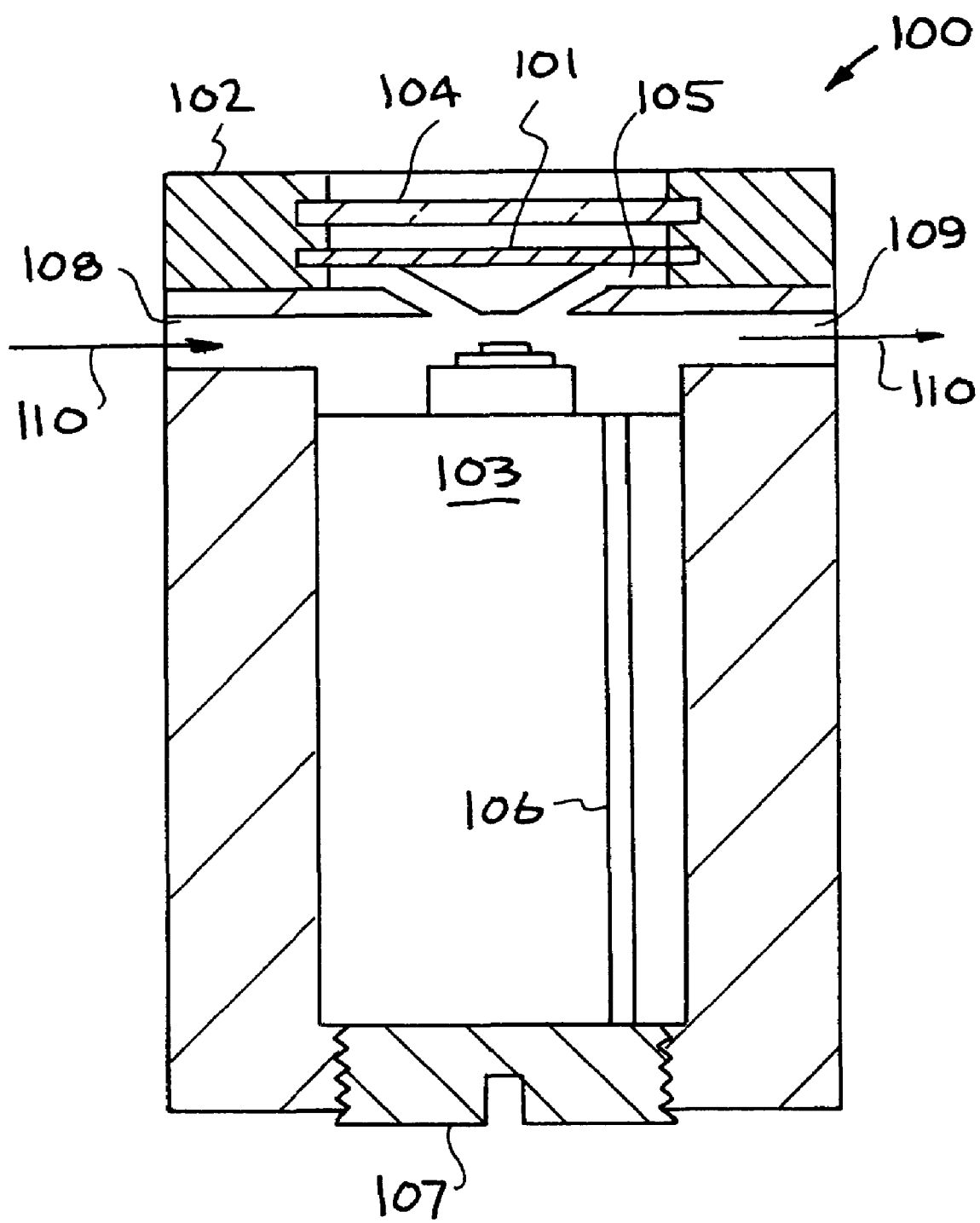
FIG. 1 illustrates a system for filtering and recovering small particles from a fluid.

Referring now to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

An embodiment of the present invention is illustrated by the system shown in FIG. 1. The system is designated generally by the reference numeral 100. The system 100 provides an apparatus and method for filtering particles from a fluid. A fluid 110 containing the particles is directed to a barrier channel. The dimensions of the barrier channel are varied to physically trap particles of a desired size without stopping fluid flow.

The system 100 has uses in any field where in-line filtering and recovering of particles from 1–500 microns in size is desirable. Examples of use of the system 100 include environmental monitoring applications, biomedical sample preparation, and any other industrial process that requires particle filtration. Specific examples include, the following:

Bead-based Assays—Many current biological and chemical assays use beads as assay templates for concentrating, reacting, and purifying various reaction components. Beads are the most commonly used platform for automating otherwise labor-intensive lab bench protocols. Sample can be captured, via antibody/antigen reactions, on bead surfaces. Trapping of the beads allows undesirable background particles and substances to be removed from the sample. Addition of subsequent reactants (such as optically labeled tags) and proceeded by alternately trapping, washing, and recovering of the beads.

Filtration of Target Bioagents—Spores, bacteria, white blood cells, and similar biological agents over 1 micron in size can be selectively captured using the system 100. Capturing spores or bacteria allows preconcentration (filtration with subsequent recover) of these species from a sample volume. This is particularly desirable in environmental monitoring applications for highly virulent species such as anthrax, where preconcentration of the target agent can result in increased assay sensitivity. The system 100, also allows separation of plasma from whole blood, while retaining the ability to re-elute the blood cells.

The system 100 provides for filtering and recovering small particles from a fluid using a variable, flexure-based trap. A particle-containing fluid 110 is introduced through the feed inlet 108, then flowed through a barrier channel to an outlet channel 109. The dimensions of the barrier channel can reduced, via a flexure-based method, to physically trap particles of various sizes without stopping fluid flow to the outlet channel. Following filtration, the size of the barrier channel can then be increased, allowing recovery of the trapped particles.

The present invention provides an apparatus and method for filtering particles from a fluid. In one embodiment an apparatus is provided for filtering particles from a fluid. The apparatus comprises a fluid inlet, a fluid outlet, a variable size passage between the fluid inlet and the fluid outlet, and means for adjusting the size of the variable size passage for filtering the particles from the fluid. In one embodiment the means for adjusting the size of the variable size passage is a piezo-electric stack. In another embodiment the means for adjusting the size of the variable size passage is a piezo-electric stack and a strain gauge is operatively connected to the piezo-electric stack. In another embodiment the means for adjusting the size of the variable size passage is a piezo-electric stack and a set screw operatively connected to the piezo-electric stack. In one embodiment a window is operatively connected to the variable size passage. In another embodiment the window is a sapphire window.

In one embodiment the particles are from 1 micron to 500 microns in size. In another embodiment the particles are beads. In another embodiment the particles are beads and the beads include optically labeled tags. In another embodiment the particles are beads and the beads include surfaces and antibody/antigen reactions are connected to the bead surfaces.

The structural components of the variable flexure-based fluid filter system 100 include a stainless steel flexure 101 sandwiched between a metal retaining ring 102 and a piezo-electric stack 103. A sapphire window 104 is also held in place by the metal retaining ring 102, and opposes the flexure 101. This window 104 allows for visual inspection of the particle sequestering area 105 during operation and creates the gap that determines the size of particle that will be filtered or trapped. Particles can be released, on demand, by varying the gap between the flexure and the window. The piezo-electric stack 103 is equipped with a strain gauge 106 that provides feed back on the deflection of the stack 103 and indicates gap distance. The variable flexure-based fluid filter 100 is equipped with an inlet 108 and an outlet 109. Fluid 110 enters the flexure 101 via the inlet 108 at the bottom of a conical region in the center of the flexure 101. A circular barrier traps particles in the conical region.

Operation of the system 100 will now be described. Initial loading on the flexure 101 is obtained by tightening a set screw 107 at the bottom of the piezo-electric stack 103 with the stack 103 contracted until some deflection in the strain gauge 106 is recorded. This establishes the minimum limit at which intimate contact between the piezo-electric stack 103 and the flexure has been established. To establish the maximum expansion limit, the stack 103 is expanded until a colored dye solution in water will not pass across the particle barrier. In this position the barrier was in tight contact with the sapphire window 104 and no liquid could pass. The gap of interest is set from the known deflection of 7.55 gm/volt. This value can be verified experimentally using polystyrene latex calibration beads.

Figure 2:
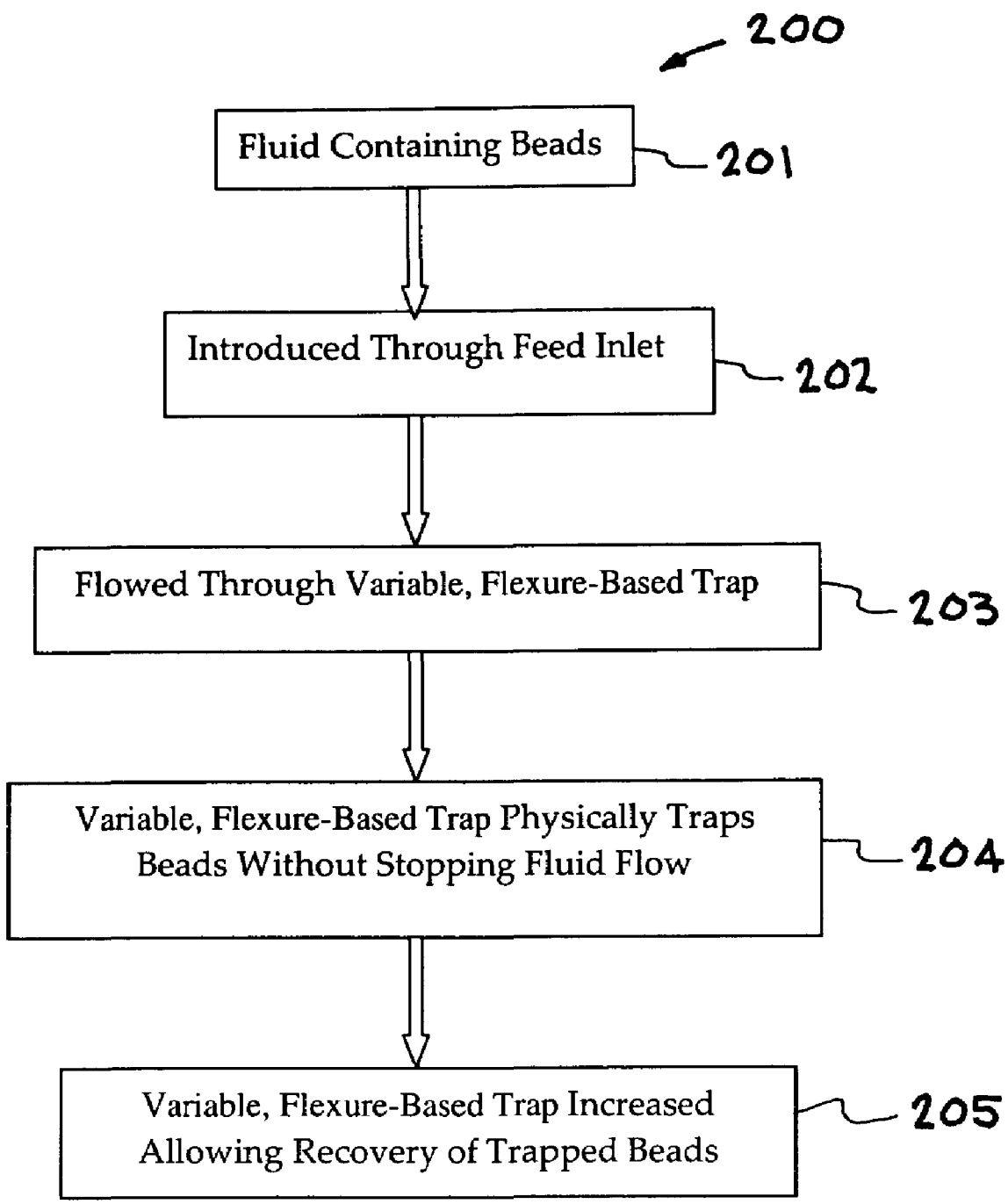
FIG. 2 illustrates another embodiment of the invention with a system for filtering and recovering small beads from a fluid.

Referring now to FIG. 2, another embodiment of a system for filtering and recovering small particles from a fluid is illustrated. Referring now to FIG. 2, a system for filtering and recovering beads from a fluid using a variable, flexure-based trap is illustrated. The system is designated generally by the reference numeral 200. Many current biological and chemical assays use beads as assay templates for concentrating, reacting, and purifying various reaction components. Beads are the most commonly used platform for automating otherwise labor-intensive lab bench protocols. Sample can be captured, via antibody/antigen reactions, on bead surfaces. Trapping of the beads allows undesirable background particles and substances to be removed from the sample. Addition of subsequent reactants (such as optically labeled tags) and proceeded by alternately trapping, washing, and recovering of the beads.

A fluid containing the beads 201 is used. Initially, the fluid is introduced through a feed inlet 202. In the next step, the fluid is flowed through a variable, flexure-based trap 203. In the next step, the variable, flexure-based trap physically trap beads without stopping fluid flow 204. In the next step, the variable, flexure-based trap is increased allowing recovery of the trapped beads.

Referring now to FIGS. 1 and 2, the system 200 for filtering particles from a fluid using a variable, flexure-based trap 100 as illustrated in FIG. 1 will be described. In one embodiment the present invention provides a method of filtering and recovering particles from a fluid. The method comprises the steps of introducing an inlet fluid flow stream to a fixture with a variable size passage, and setting the size of the variable size passage so that the fluid passes through the variable size passage but the particles do not pass through the variable size passage. In one embodiment the step of setting the size of the variable size passage is accomplished using a piezo-electric stack. In another embodiment the step of setting the size of the variable size passage is accomplished using a piezo-electric stack and a strain gauge operatively connected to the piezo-electric stack. In another embodiment the step of setting the size of the variable size passage is accomplished using a piezo-electric stack and a set screw operatively connected to the piezo-electric stack.

In one embodiment the step of setting the size of the variable size passage is accomplished using a piezo-electric stack and a window operatively connected to the variable size passage. In another embodiment the particles are from 1 micron to 500 microns in size. In another embodiment the particles are beads. In another embodiment the particles are beads and the method includes the step of attaching optically labeled tags to the beads. In another embodiment the particles are beads. In another embodiment the particles are beads and the method includes the step of attaching antibody/antigen reactions to the beads. In another embodiment the particles are beads. In another embodiment the particles are beads and the method includes the step of eluting the particles using an outlet flow stream. In another embodiment the particles are beads. In another embodiment the particles are beads and the method includes the step of capturing the beads using an outlet flow stream.

Initial loading on the flexure 101 is obtained by tightening a set screw 107 at the bottom of the piezo-electric stack 103 with the stack 103 contracted until some deflection in the strain gauge 106 is recorded. This establishes the minimum limit at which intimate contact between the piezo-electric stack 103 and the flexure has been established. To establish the maximum expansion limit, the stack 103 is expanded until a colored dye solution in water will not pass across the bead barrier. To establish the maximum expansion limit, the stack is expanded until a colored dye solution in water will not pass across the barrier. In this position the barrier was in tight contact with the sapphire window and no liquid could pass.

The dimensions of the barrier channel can reduced, via a flexure-based method, to physically trap beads of various sizes without stopping fluid flow to the outlet channel. The piezo-electric stack is expanded to the position determined experimentally to allow the passage of liquid but not calibration beads. Then the liquid sample with suspended beads is introduced and flows over the bead barrier into a circular moat leaving the beads trapped in the conical region. The fluid continues via the outlet to waste. To access the beads for subsequent manipulation, the flexure is relaxed and the beads are drawn from the; flexure with liquid that now flows unimpeded over the bead barrier. Following filtration, the size of the barrier channel can then be increased, allowing recovery of the trapped beads.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A variable flexure-based fluid filter apparatus for filtering particles from a fluid, comprising:
   a variable flexure-based fluid filter body,
   a fluid passage in said body,
   a fluid inlet connected to said fluid passage,
   a fluid outlet connected to said fluid passage,
   a flexure unit connected to said passage,
   an expandable piezo-electric stack connected to said passage and positioned proximate said flexure unit,
   a variable size passage between said flexure unit and said expandable piezo-electric stack, wherein said piezo-electric stack can be expanded for adjusting the size of said variable size passage for filtering said particles from said fluid and wherein expansion of said piezo-electric stack provides deflection of said flexure unit,
   a particle sequestering area connected to said fluid passage and located adjacent said flexure unit, said variable size passage, and said expandable piezo-electric stack, and
   a window in said body operatively connected to said particle sequestering area wherein said window allows visual inspection of said particle sequestering area.

2. The variable flexure-based fluid filter apparatus for filtering particles from a fluid of claim 1 wherein said flexure unit is a steel flexure unit.

3. The variable flexure-based fluid filter apparatus for filtering particles from a fluid of claim 1 including a strain gauge operatively connected to said piezo-electric stack and said flexure unit that provides feedback on said deflection of said flexure unit.

4. The variable flexure-based fluid filter apparatus for filtering particles from a fluid of claim 1 including a set screw operatively connected to said piezo-electric stack.

5. The variable flexure-based fluid filter apparatus for filtering particles from a fluid of claim 1 wherein said window operatively connected to said particle sequestering area is located opposite said piezo-electric stack.

6. The variable flexure-based fluid filter apparatus for filtering particles from a fluid of claim 1 wherein said window is a sapphire window.

7. The variable flexure-based fluid filter apparatus for filtering particles from a fluid of claim 1 wherein said variable size passage has a size range to accommodate particles from 1 micron to 500 microns in size.

8. The variable flexure-based fluid filter apparatus for filtering particles from a fluid of claim 1 wherein said variable size passage accommodates particles that are beads.

9. The variable flexure-based fluid filter apparatus for filtering particles from a fluid of claim 8 wherein said beads include optically labeled tags.

10. The apparatus for filtering particles from a fluid of claim 8 wherein said beads include bead surfaces and antibodies or antigens on said bead surfaces.

* * * * *